United States Patent [19]

Gross et al.

[11] Patent Number: 5,637,587
[45] Date of Patent: Jun. 10, 1997

[54] SYNERGY BIOCIDES FOR USE IN AQUEOUS ORE SLURRIES

[75] Inventors: Anthony E. Gross, St. Charles; Nancy L. Casselman, Wheaton, both of Ill.

[73] Assignee: Nalco Chemical Company, Naperville, Ill.

[21] Appl. No.: 597,791

[22] Filed: Feb. 7, 1996

[51] Int. Cl.$^6$ .......................... A01N 33/18; A01N 43/34; A01N 43/66

[52] U.S. Cl. .............. 514/244; 422/28; 422/37; 504/155; 514/727

[58] Field of Search ...................... 514/244, 727; 422/28, 37; 504/155

[56] References Cited

U.S. PATENT DOCUMENTS 5,185,355  2/1993  Hsu ........................................ 514/372
5,190,944  3/1993  Hsu ........................................ 514/244

*Primary Examiner*—Allen J. Robinson
*Attorney, Agent, or Firm*—James J. Drake; Robert A. Miller

[57] ABSTRACT

This invention provides a surprisingly efficacious combination useful for inhibiting microorganism growth, particularly in aqueous slurries containing mineral ore. In particular embodiments, the invention provides an antimicrobial composition comprising 1-(3-chloroallyl)-3,5,7 triaza-1-azoniaadamantane chloride and 2-bromo-2-nitropropane-1,3-diol. The invention also provides a method for inhibiting microbial growth in an aqueus mineral or ore slurry, e.g. a kaolin slurry. The method includes the step of adding to the slurry a microbiocidal composition of 1-(3-chloroallyl)-3,5,7 triaza-1-azoniaadamantane chloride and 2-bromo-2-nitropropane-1,3-diol.

5 Claims, No Drawings

SYNERGY BIOCIDES FOR USE IN AQUEOUS ORE SLURRIES

BACKGROUND OF THE INVENTION

1. Field of the Invention

This invention relates to methods and compositions exhibiting synergistic antimicrobial (biocidal) activity using a combination of 1-(3-chloroallyl)-3,5,7 triaza-1-azoniaadamantane chloride and 2-bromo-2-nitropropane-1,3-diol. The methods and compositions of the invention are very effective in preventing microbial spoilage of aqueous mineral and ore slurries and in paper and pulp preparation.

2. Description of the Prior Art

Various ores contain minerals that must be separated and purified to achieve their final useful state. A representative example of this type of separation process is the mining and separating of kaolin clay from the tailings. In the U.S., kaolin is mined from the middle Georgia clay belt with a dragline operation. An overburden of red soil is removed to reach the kaolin which can vary from a cream color to gray. Crude clay from various properties is sent to a crude clay storage.

The first step in the processing is called blunging. Crude clay having different properties can be blended at this point to give desired characteristics in the final product. Blunging is a high shear process used to slurry the ore at 50% to 60% solids in water. Inorganic dispersants such as hexametaphosphate, tripolyphosphate, and silicate are normally added to reduce the viscosity of the slurry. pH is adjusted to the basic side with sodium carbonate.

After the pH is adjusted, the slurry is degritted with a dragbox to remove large particles. Degritted slurry having different properties is sometime blended at this point. The crude slurry is then sent to centrifuges to reduce the size of 90% to 92% of the slurry to less than 2 µm for a fine clay. A coarse clay may be on the order of 90% of the slurry reduced to less than 75 µm.

High gradient magnetic separators are used to remove $TiO_2$ and iron oxide impurities from the crude slurry. Magnetic strength is 1.5 to 2.0 tesla. If desired, the clay is then delaminated in attrition mills. If a clay has a high organic content, it is treated with ozone at this point for color reduction. Next, the clay is leached with sodium bisulfite at pH≦3. Ferric iron is reduced to ferrous and brought into solution. The leached slurry is then filtered and ferrous iron removed in the filtrate. In the next step, a portion of the filter cake is redispersed in water using organic dispersants. Biocides may be added in both the filtration and dispersing steps.

A second portion of the filter cake is spray dried and the final product is made by combining the blunged filter cake with spray dried material to give about a 70% solids product. Additional dispersant and biocide is often added at this time.

Known biocidal compositions have been either unsuccessful or uneconomical in removing microbiological contamination from these ore and mineral processing slurries. Accordingly, a biocide capable of economically removing microbiological contaminants without adversely affecting the final clay product is desired.

SUMMARY OF THE INVENTION

This invention provides a surprisingly efficacious combination useful for inhibiting microorganism growth, particularly in aqueous slurries containing minerals. In particular embodiments, the invention provides an antimicrobial composition comprising 1-(3-chloroallyl)-3,5,7 triaza-1-azoniaadamantane chloride and 2-bromo-2-nitropropane-1,3-diol. The invention also provides a method for inhibiting microbial growth in an aqueous mineral or ore slurry, e.g. a kaolin slurry. The method includes the step of adding to the slurry a microbiocidal composition of 1-(3-chloroallyl)-3,5,7 triaza-1-azoniaadamantane chloride and 2-bromo-2-nitropropane-1,3-diol.

DESCRIPTION OF THE PREFERRED EMBODIMENTS

The method comprises a composition combining 1-(3-chloroallyl)-3,5,7 triaza-1-azoniaadamantane chloride and 2-bromo-2-nitropropane-1,3-diol in a ratio ranging from 0.001 parts per million, (hereinafter ppm) 1-(3-chloroallyl)-3,5,7 triaza-1-azoniaadamantane chloride to 1 ppm 2-bromo-2-nitropropane-1,3-diol to 100 ppm 1-(3-chloroallyl)-3,5,7 triaza-1-azoniaadamantane chloride to 1 ppm 2-bromo-2-nitropropane-1,3-diol.

The invention further comprises a method of inhibiting microbiological growth in mineral and ore slurries comprising of adding to the slurry a microbiocidal combination composition of 1-(3-chloroallyl)-3,5,7 triaza-1-azoniaadamantane chloride and 2-bromo-2-nitropropane-1,3-diol in a ratio ranging from 0.001 ppm 1-(3-chloroallyl)-3,5,7 triaza-1-azoniaadamantane chloride to 1 part 2-bromo-2-nitropropane-1,3-diol to 100 ppm 1-(3-chloroallyl)-3,5,7 triaza-1-azoniaadamantane chloride to 1 ppm 2-bromo-2-nitropropane-1,3-diol, in amounts of each which in combination, are effective to inhibit microbial growth.

The synergistic anti-microbial composition of the present invention may find utility in a variety of applications in which biocides are commonly used including, e.g., applications in industries that make or use paper, wood and pulp and their products and in the latex industry, e.g., in preparation of paints and other coatings. In general, the synergistic anti-microbial composition can be utilized in any aqueous system having suitable conditions conducive to the growth of microorganisms. However, a particularly important contribution of the synergistic anti-microbial composition is to the ore and mineral processing industry, to prevent microbial growth, putrification and/or destabilization of aqueous ore and mineral slurries. Accordingly, without limiting the invention in any way, the use of the synergistic anti-microbials of the present invention in this context is described below.

In a preferred embodiment, a synergistic combination of 1-(3-chloroallyl)-3,5,7 triaza-1-azoniaadamantane chloride and 2-bromo-2-nitropropane-1,3-diol is used for protection of an aqueous mineral slurry formulated for use in a papermaking facility. The combination of these agents may be used in protection of any of a number of ore and mineral slurries used in the papermaking industry.

Among other things, the methods of the invention may be used to treat aqueous ore and mineral slurries such as kaolin, which are formulated for use in papermaking and similar applications. A composition for use in papermaking comprises kaolin, various other mineral fillers and one or more dispersants and 1-(3-chloroallyl)-3,5,7 triaza-1-azoniaadamantane chloride and 2-bromo-2-nitropropane-1,3-diol in amounts of each that, in combination, are effective to inhibit microbial growth in the slurry is also claimed.

The following example is presented to describe preferred embodiments and utilities of the invention and are not meant to limit the invention unless otherwise stated in the claims appended hereto.

EXAMPLE

Plant slurry samples were obtained from two kaolin ore processing facilities for biocide screening. Tests were set up to determine the synergistic effects of various treatments. In formulations containing 10% 2-bromo-2-nitropropane-1,3-diol (Compound A), isothiazolin (Compound B) and peroxide were used in combination with 1-(3-chloroallyl)-3,5,7 triaza-1-azoniaadamantane chloride (Compound C), as well as tested alone. The goal of the tests was to determine the lowest active doses required to achieve quick kill properties followed by preservative effects. Three samples were obtained from Facility A, while one sample from Facility B was used.

Results showed that while Compound C alone was not effective on contaminated slurry, it showed positive longer term results when used in combination with other biocides.

Facility A—Sample 1

The Compound B/Compound C (600/50) blends showed considerable growth. (Table I)
Blends of peroxide/Compound C had no growth at 75/75 ppm and above. Dosages below these levels contained bacterial growth.
Compound A/Compound C (12.5/12.5) at the lowest blended dose still showed no signs of contamination.
Compound C and Compound B alone had significant colonies, while Compound A (25) had none.

Facility A—Sample 2

This slurry at pH 5.9, had no colony growth with the Compound B/Compound C blend at the lowest treatment levels. Compound B (100, 200 & 400 ppm), and Compound A (50, 75 ppm) also had no growth. (Table II)
Compound C (75, 100 ppm) and Compound A (12.5, 25 ppm) had significant growth while the combination of Compound A/Compound C (12.5,12.5) had no growth as well as the Compound B/Compound C combination at the lowest dose (100/12.5).

Facility A—Sample 3

This slurry showed no growth at all the low dosages. (Table III)

Facility B

Slurry, with a pH of 6.92, showed no growth at all low dosages. (Table IV)

TABLE I

FACILITY A - SAMPLE 1

| TREATMENT 14-June | DOSE (PPM) | FILM 21-June | FILM 28-June |
|---|---|---|---|
| PEROXIDE(3%)/Compound C | 200/12.5 | | negX10E3 |
| | 200/25 | | negX10E3 |
| | 200/50 | | negX10E3 |
| | 200/75 | | negX10E3 |
| | 100/12.5 | | negX10E3 |
| | 100/25 | | negX10E3 |
| | 100/50 | | negX10E3 |
| | 100/75 | | negX10E3 |
| | 75/12.5 | | 3.6X10E6 |
| | 75/25 | | 4.5X10E4 |
| | 75/50 | | negX10E3 |
| | 75/75 | | negX10E3 |
| | 50/12.5 | | growth |
| | 50/25 | | growth |
| | 50/50 | | negX10E3 |
| | 50/75 | | 1.1X10E7 |
| | 25/12.5 | TNTCX10E4 | |
| | 25/25 | 3X10E6 | |
| | 25/50 | 1.4X10E7 | |
| | 25/75 | 1.5X10E7 | |
| Compound B/Compound C | 1200/12.5 | | |
| | 1200/25 | | |
| | 1200/50 | | |
| | 800/12.5 | | |
| | 800/25 | | |
| | 800/50 | | |
| | 600/12.5 | | TNTCX10E4 |
| | 600/25 | | TNTCX10E4 |
| | 600/50 | | TNTCX10E4 |
| | 400/12.5 | | TNTCX10E4 |
| | 400/25 | | TNTCX10E4 |
| | 400/50 | | TNTCX10E4 |
| | 200/12.5 | | TNTCX10E4 |
| | 200/25 | | TNTCX10E4 |
| | 200/50 | | TNTCX10E4 |
| | 100/12.5 | TNTCX10E4 | TNTCX10E4 |
| | 100/25 | TNTCX10E4 | TNTCX10E4 |
| | 100/50 | TNTCX10E4 | TNTCX10E4 |
| CONTROL | | TNTCX10E4 | 1.1X10E8 |
| Compound A/Compound C | 12.5/12.5 | negX10E3 | negX10E3 |
| | 12.5/25 | negX10E3 | negX10E3 |
| | 12.5/50 | negX10E3 | negX10E3 |
| | 25/12.5 | negX10E3 | negX10E3 |
| | 25/25 | negX10E3 | negX10E3 |

TABLE I-continued

| | FACILITY A - SAMPLE 1 | | |
|---|---|---|---|
| TREATMENT 14-June | DOSE (PPM) | FILM 21-June | FILM 28-June |
| | 25/50 | negX10E3 | negX10E3 |
| | 50/12.5 | | negX10E3 |
| | 50/25 | | negX10E3 |
| | 50/50 | | negX10E3 |
| | 75/12.5 | | |
| | 75/25 | | |
| | 75/50 | | |
| | 100/12.5 | | |
| | 100/25 | | |
| | 100/50 | | |
| | 200/12.5 | | |
| | 200/25 | | |
| | 200/50 | | |
| Compound C | 75 | TNTCX10E4 | |
| | 100 | TNTCX10E4 | |
| | 150 | | TNTCX10E4 |
| | 200 | | TNTCX10E4 |
| Compound A | 12.5 | negX10E3 | 2.7X10E4 |
| | 25 | negX10E3 | negX10E3 |
| | 50 | negX10E3 | negX10E3 |
| | 75 | negX10E3 | negX10E3 |
| Compound B | 100 | TNTCX10E4 | 7.2X10E7 |
| | 200 | TNTCX10E4 | 5.6X10E7 |
| | 400 | TNTCX10E4 | 4.4X10E7 |
| | 600 | | TNTCX10E4 |
| | 800 | | TNTCX10E4 |
| | 1200 | | TNTCX10E4 |

TABLE II

| | FACILITY A - SAMPLE 2 | | |
|---|---|---|---|
| TREATMENT 6/13, pH: 5.9 | DOSE (PPM) | FILM 21-June | FILM 30-June |
| PEROXIDE(3%)/Compound C | 600/12.5 | | |
| | 600/25 | | |
| | 600/50 | | |
| | 600/75 | | |
| | 100/12.5 | | 4.6X10E6 |
| | 100/25 | | 4.4X10E6 |
| | 100/50 | | 2.6X10E6 |
| | 100/75 | | 1.4X10E6 |
| | 75/12.5 | | 2.2X10E7 |
| | 75/25 | | 1.6X10E7 |
| | 75/50 | | 1.6X10E6 |
| | 75/75 | | 1.4X10E7 |
| | 50/12.5 | | 1.4X10E6 |
| | 50/25 | | 2X10E7 |
| | 50/50 | | 8.4X10E6 |
| | 50/75 | | 6.2X10E6 |
| | 25/12.5 | 1.2X10E7 | |
| | 25/25 | 8X10E6 | |
| | 25/50 | 5.6X10E6 | |
| | 25/75 | 8X10E6 | |
| Compound B/Compound C | 1200/12.5 | | |
| | 1200/25 | | |
| | 1200/50 | | |
| | 800/12.5 | | |
| | 800.25 | | |
| | 800.50 | | |
| | 600/12.5 | | |
| | 600/25 | | |
| | 600/50 | | |
| | 400/12.5 | | negX10E3 |
| | 400/25 | | negX10E3 |
| | 400/50 | | negX10E3 |
| | 200/12.5 | | negX10E3 |
| | 200/25 | | negX10E3 |
| | 200/50 | | negX10E3 |
| | 100/12.5 | negX10E3 | negX10E3 |
| | 100/25 | negX10E3 | negX10E3 |
| | 100/50 | negX10E3 | negX10E3 |

TABLE II-continued

FACILITY A - SAMPLE 2

| TREATMENT 6/13, pH: 5.9 | DOSE (PPM) | FILM 21-June | FILM 30-June |
|---|---|---|---|
| CONTROL | | 6.6X10E6 | 3.2X10E7 |
| Compound A/Compound C | 12.5/12.5 | negX10E3 | 8.8X10E6 |
| | 12.5/25 | negX10E3 | 3.8X10E6 |
| | 12.5/50 | negX10E3 | 4.6X10E6 |
| | 25/12.5 | negX10E3 | 3.6X10E6 |
| | 25/25 | negx10E3 | 2.2X10E6 |
| | 25/50 | negX10E3 | 2.4X10E5 |
| | 50/12.5 | negX10E3 | 3.1X10E5 |
| | 50/25 | negX10E3 | 1.2X10E5 |
| | 50/50 | negX10E3 | 1.8X10E5 |
| | 75/12.5 | | |
| | 75/25 | | |
| | 75/50 | | |
| | 100/12.5 | | |
| | 100/25 | | |
| | 100/50 | | |
| | 200/12.5 | | |
| | 200/25 | | |
| | 200/50 | | |
| Compound C | 75 | 6X10E6 | |
| | 100 | 4X10E6 | |
| | 150 | | |
| | 200 | | |
| Compound A | 12.5 | 1.4X10E6 | |
| | 25 | 3.8X10E5 | |
| | 50 | negX10E3 | |
| | 75 | negX10E3 | |
| Compound B | 100 | negX10E3 | |
| | 200 | negX10E3 | |
| | 400 | negX10E3 | |
| | 600 | | |
| | 800 | | |
| | 1200 | | |

TABLE III

FACILITY A - SAMPLE 3

| TREATMENT | DOSE (PPM) | FILM 20-June | FILM |
|---|---|---|---|
| PEROXIDE(3%)Compound C | 600/12.5 | | |
| | 600/25 | | |
| | 600/50 | | |
| | 600/75 | | |
| | 100/12.5 | | |
| | 100/25 | | |
| | 100/50 | | |
| | 100/75 | | |
| | 75/12.5 | | |
| | 75/25 | | |
| | 75/50 | | |
| | 75/75 | | |
| | 50/12.5 | | |
| | 50/25 | | |
| | 50/50/ | | |
| | 50/75 | | |
| | 25/12.5 | negX10E3 | |
| | 25/25 | negX10E3 | |
| | 25/50 | negX10E3 | |
| | 25/75 | negX10E3 | |
| Compound B/Compound C | 1200/12.5 | | |
| | 1200/25 | | |
| | 1200/50 | | |
| | 800/12.5 | | |
| | 800.25 | | |
| | 800.50 | | |
| | 600/12.5 | | |
| | 600/25 | | |
| | 600/50 | | |
| | 400/12.5 | | |
| | 400/25 | | |
| | 400/50 | | |

TABLE III-continued

FACILITY A - SAMPLE 3

| TREATMENT | DOSE (PPM) | FILM 20-June | FILM |
|---|---|---|---|
|  | 200/12.5 |  |  |
|  | 200/25 |  |  |
|  | 200/50 |  |  |
|  | 100/12.5 | negX10E3 |  |
|  | 100/25 | negX10E3 |  |
|  | 100/50 | negX10E3 |  |
| CONTROL |  | negX10E3 |  |
| Compound A/Compound C | 12.5/12.5 | negX10E3 |  |
|  | 12.5/25 | negX10E3 |  |
|  | 12.5/50 | negX10E3 |  |
|  | 25/12.5 | negX10E3 |  |
|  | 25/25 | negX10E3 |  |
|  | 25/50 | negX10E3 |  |
|  | 50/12.5 |  |  |
|  | 50/25 |  |  |
|  | 50/50 |  |  |
|  | 75/12.5 |  |  |
|  | 75/25 |  |  |
|  | 75/50 |  |  |
|  | 100/12.5 |  |  |
|  | 100/25 |  |  |
|  | 100/50 |  |  |
|  | 200/12.5 |  |  |
|  | 200/25 |  |  |
|  | 200/50 |  |  |
| Compound C | 75 | negX10E3 |  |
|  | 100 | negX10E3 |  |
|  | 150 |  |  |
|  | 200 |  |  |
| Compound A | 12.5 | negX10E3 |  |
|  | 25 | negX10E3 |  |
|  | 50 | negX10E3 |  |
|  | 75 | negX10E3 |  |
| Compound B | 100 | negX10E3 |  |
|  | 200 | negX10E3 |  |
|  | 400 | negX10E3 |  |
|  | 600 |  |  |
|  | 800 |  |  |
|  | 1200 |  |  |

TABLE IV

FACILITY B

| TREATMENT 6/15, pH: 6.92 | DOSE (PPM) | FILM 23-June | FILM 26-June |
|---|---|---|---|
| PEROXIDE(3%)/ | 200/75 | negX10E3 |  |
| Compound C | 200/100 | negX10E3 |  |
|  | 200/150 | negX10E3 |  |
|  | 200/200 | negX10E3 |  |
|  | 100/75 | negX10E3 |  |
|  | 100/100 | negX10E3 |  |
|  | 100/150 | negX10E3 |  |
|  | 100/200 | negX10E3 |  |
| PEROXIDE(3%)/ | 200/75 |  |  |
| Compound A | 200/100 |  |  |
|  | 200/150 |  |  |
|  | 200/200 |  |  |
|  | 100/75 | negX10E3 |  |
|  | 100/100 | negX10E3 |  |
|  | 100/150 | negX10E3 |  |
|  | 100/200 | negX10E3 |  |
| UCARCIDE/Compound C | 200/75 |  |  |
|  | 200/100 |  |  |
|  | 200/150 |  |  |
|  | 200/200 |  |  |
|  | 100/75 | negX10E3 |  |
|  | 100/100 | negX10E3 |  |
|  | 100/150 | negX10E3 |  |
|  | 100/200 | negX10E3 |  |
| UCARCIDE/Compound A | 200/75 |  |  |
|  | 200/100 |  |  |
|  | 200/150 |  |  |
|  | 200/200 |  |  |
|  | 100/75 |  |  |
|  | 100/100 | negX10E3 |  |
|  | 100/150 | negX10E3 |  |
|  | 100/200 | negX10E3 |  |
| CONTROL |  |  | 1x10E5 |
| Compound A/Compound C | 25/12.5 |  | negX10E3 |
|  | 25/25 |  | negX10E3 |
|  | 25/50 |  | negX10E3 |
|  | 50/12.5 |  | negX10E3 |
|  | 50/25 |  | negX10E3 |
|  | 50/50 |  | negX10E3 |
|  | 75/12.5 |  |  |
|  | 75/25 |  |  |
|  | 75/50 |  |  |
|  | 100/12.5 |  |  |
|  | 100/25 |  |  |
|  | 100/50 |  |  |
| Compound C | 75 |  | negX10E3 |
|  | 100 |  | negX10E3 |
|  | 150 |  |  |

TABLE IV-continued

| | FACILITY B | | |
|---|---|---|---|
| TREATMENT 6/15, pH: 6.92 | DOSE (PPM) | FILM 23-June | FILM 26-June |
| | 200 | | |
| Compound A | 12.5 | | negX10E3 |
| | 25 | | negX10E3 |
| | 50 | | negX10E3 |
| | 75 | | negX10E3 |
| UCARCIDE | 400 | | negX10E3 |
| | 600 | | negX10E3 |
| | 800 | | negX10E3 |

Additional tests were run to verify the performance of the biocide composition of this invention on kaolin clay samples obtained at Facility A. These tests were run at a different time than the test set forth above using similar kaolin clay slurries. Results are set forth on Tables V and VI below.

TABLE V

| SAMPLE | TREATMENT | DOSE (PPM) |
|---|---|---|
| 1 FACILITY A - SAMPLE 4 | Compound A/Compound C | 10/10 |
| 2 FACILITY A - SAMPLE 4 | Compound A/Compound C | 15/10 |
| 3 FACILITY A - SAMPLE 4 | Compound A/Compound C | 20/10 |
| 4 FACILITY A - SAMPLE 4 | Compound A/Compound C | 51/10 (Compound C added dry) |
| 5 FACILITY A - SAMPLE 4 | control | 0 |
| 6 FACILITY A - SAMPLE 4 | Compound A/Compound C | 20/180 |
| 7 FACILITY A - SAMPLE 4 | Compound A/Compound C | 35/315 |
| 8 FACILITY A - SAMPLE 4 | Compound A | 192.4 |
| 9 FACILITY A - SAMPLE 4 | Compound A/Compound C | 144.2/146.2 |
| 10 FACILITY A - SAMPLE 4 | Compound A/Compound C | 96.2/292 |
| 11 FACILITY A - SAMPLE 4 | Compound A/Compound C | 48/438 |
| 12 FACILITY A - SAMPLE 4 | Compound C | 584 |

| Sample | film 10/18 | film 10/24 | film 11/1 |
|---|---|---|---|
| 1 FACILITY A - SAMPLE 4 | — | — | — |
| 2 | — | — | — |
| 3 | — | — | — |
| 4 | — | — | — |
| 5 | 79E7 | — | — |
| 6 | 44E6 | 40E6 | — |
| 7 | negE3 | negE3 | negE2 |
| 8 | 12E6 | 90E5 | 70E5 |
| 9 | negE3 | negE3 | negE2 |
| 10 | negE3 | negE3 | negE2 |
| 11 | negE3 | negE3 | negE2 |
| 12 | negE3 | negE3 | — |

Inoculated with 2.4E6 colonies to 100 cc each

| Sample | film 10/24 | film 11/1 | |
|---|---|---|---|
| 1 FACILITY A - SAMPLE 4 | — | — | — |
| 2 | — | — | — |
| 3 | — | — | — |
| 4 | — | — | — |
| 5 | 70E6 | — | — |
| 6 | 300E6 | — | — |
| 7 | negE3 | negE2 | |
| 8 | 200E5 | 240E5 | |
| 9 | TNTCE4 | negE2 | |
| 10 | negE3 | negE2 | |
| 11 | negE3 | negE2 | |
| 12 | negE3 | — | |

TABLE VI

| SAMPLE | TREATMENT | DOSE (ppm) |
|---|---|---|
| 5 FACILITY A - SAMPLE 5 | control | 0 |
| 6 FACILITY A - SAMPLE 5 | Compound A/Compound C | 10/90 |

TABLE VI-continued

| | | |
|---|---|---|
| 7 FACILITY A - SAMPLE 5 | Compound A/Compound C | 17.5/157.5 |
| 8 FACILITY A - SAMPLE 5 | Compound A/ | 96.2 |
| 9 FACILITY A - SAMPLE 5 | Compound A/Compound C | 72.1/73.1 |
| 10 FACILITY A - SAMPLE 5 | Compound A/Compound C | 48.1/146 |
| 11 FACILITY A - SAMPLE 5 | Compound A/Compound C | 24/219 |
| 12 FACILITY A - SAMPLE 5 | Compound C | 292 |
| 12A FACILITY A - SAMPLE 5 | Compound A/Compound C | 48.1/292 |
| 12B FACILITY A - SAMPLE 5 | Compound A/Compound C | 48.1/146 |

| Sample | film 10/18 | film 10/24 | film 11/1 |
|---|---|---|---|
| 5 FACILITY A - SAMPLE 5 | 42E6 | 300E5 | 300E5 |
| 6 | 29E5 | 80E4 | 80E4 |
| 7 | negE2 | TNTCE3 | 10E4 |
| 8 | negE2 | negE2 | negE2 |
| 9 | negE2 | negE2 | negE2 |
| 10 | negE2 | negE2 | negE2 |
| 11 | negE2 | negE2 | negE2 |
| 12 | — | — | — |
| 12A | negE3 | negE2 | negE2 |
| 12B | — | 40E4 | |

Inoculated with 4.2E6 to 100 cc each

| Sample | film 10/24 | film 11/1 |
|---|---|---|
| 5 FACILITY A - SAMPLE 5 | — | — |
| 6 | 260E5 | — |
| 7 | negE3 | 10E4 |
| 8 | negE3 | negE2 |
| 9 | negE3 | negE2 |
| 10 | negE3 | negE2 |
| 11 | negE3 | negE2 |
| 12 | — | — |
| 12A | negE3 | 40E2 |
| 12B | 800E5 | — |

Acutal buckets opened and plated after 8 weeks

| Sample | film 11/7 |
|---|---|
| 5 FACILITY A - SAMPLE 5 | 700E4 |
| 6 | negE4 |
| 7 | 28E3 |
| 8 | 20E3 |
| 9 | negE2 |
| 10 | negE2 |
| 11 | negE2 |
| 12 | 180E5 |
| 12A | negE3 |
| 12B | negE3 |

The results clearly show the synergistic effect of the biocide combination of the subject invention. In Table V below tests were run in buckets. In these tests, samples of the kaolin were collected in a bucket and treated with the biocide dosages specified in the Table. The buckets were sealed with a lid, and allowed to stand for 8 weeks at ambient outdoor temperature at facility A which is located in the south eastern portion of the United States. After 8 weeks, the buckets were opened, samples collected, and plated on Petri Film available from the 3M Company, incubated and the colonies were calculated in accordance with instructions provided by the manufacturer of the Petri Film material. Results are reported on the Table.

With regard to the results shown on Tables I–V, these tests were conducted by adding a sample of the kaolin slurry to a sterile plastic bag able to hold a 100 ml sample of slurry, adding the appropriate biocide combination and dosage to the slurry contained in the bag, allowing the bag to sit for the periods of time specified in the Table, withdrawing a sample of the slurry at various time periods, plating the sample onto Petri Film, incubating and calculating the colony growth as specified above for Table VI.

The biocides used in this invention may be added to the kaolin or ore slurry either together or separately so long as both of the biocides are present in the kaolin, mineral, or ore slurry. The biocides of this invention may be added to the kaolin, mineral, or ore slurry over a wide range of ratios and dosages. Preferably, when the two biocides are added separately, the time between which the first biocide is added and the second biocide is added should be less than 24 hours.

C and A are generally used at a ratio of from 1:100 to 100:1 and preferably from 1:25 to 25:1. In a still further embodiment of the invention, the ratio of C to A is from 1:10 to 10:1 and even more preferably, from 1:5 to 2:1.

The biocide combinations are added to the slurries of the mineral, ore or kaolin so as to provide both a quick kill of organisms existing in the slurry, but also to provide for continued preservation of the slurry so as to prevent discoloration, the development of offensive odors, increases in viscosity, objectionable bacterial and algal growth, and the like which could render finished slurry compositions unfit for their intended use such as in papermaking, paints, coatings, and the like.

The biocide combinations are added to the mineral, ore, or kaolin slurry at a level so as to provide a dosage that is effective in preserving the slurry. The dosage of the biocide combination added to the slurry may vary substantially, and may range from as little as a few parts per billion of the biocide combination to as much as 1 to 10% by weight of the slurry composition in exceptional situations. Normally, from 0.1 to 1000 ppm of the biocide combination is utilized (as active ingredients), and preferably from 1 to 750 ppm of the biocide combination is utilized in the mineral, ore, or kaolin slurry. Preferably from 10 to 500 ppm of the biocide combination is utilized in the mineral, ore, or kaolin slurry based on the total weight of the mineral, ore, or kaolin contained in the slurry.

As stated above, when the biocides of this invention are used in combination with each other they may be added to the ore, mineral or kaolin slurry separately or in combination. Combinations of the biocide products may be conveniently prepared by simply mixing the two biocides together in an appropriate mixing container. Methods of mixing the two biocides will be readily apparent to those skilled in the art.

The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and the spirit of the invention.

Changes can be made in the composition, operation and arrangement of the method of the present invention described herein without departing from the concept and scope of the invention as defined in the following claims:

We claim:

1. An anti-microbial composition comprising synergistic microbicidally effective amount of 1-(3-chloroallyl)-3,5,7 triaza-1-azoniaadamantane chloride and 2-bromo-2-nitropropane-1,3-diol in a ratio ranging from about 0.001 parts 1-(3-chloroallyl)-3,5,7 triaza-1-azoniaadamantane chloride to 1 part 2-bromo-2-nitropropane-1,3-diol to about 100 parts 1-(3-chloroallyl)-3,5,7 triaza-1-azoniaadamantane chloride to 1 part 2-bromo-2-nitropropane-1,3-diol.

2. A method for inhibiting microbial growth in an aqueous ore slurry comprising adding to the slurry a synergistic microbicidally effective amount of a composition of 1-(3-chloroallyl)-3,5,7 triaza-1-azoniaadamantane chloride and 2-bromo-2-nitropropane-1,3-diol in a ratio ranging from 0.001 parts to 1 part 2-bromo-2-nitropropane-1,3-diol to 10 parts 1-(3-chloroallyl)-3,5,7 triaza-1-azoniaadamantane chloride to 1 part 2-bromo-2-nitropropane-1,3-diol.

3. The method of claim 2 wherein the dosage of the composition is from about 1 part per million to about 1000 parts per million.

4. The method of claim 3 wherein the dosage of the composition is from about 1 part per million to about 750 parts per million.

5. The method of claim 4 wherein the dosage of the composition is from about 10 parts per million to about 500 parts per million.

* * * * *